(12) United States Patent
Potrawa et al.

(10) Patent No.: US 7,399,434 B2
(45) Date of Patent: *Jul. 15, 2008

(54) RARE METAL COMPOUNDS AND MIXTURES OF THESE

(75) Inventors: Thomas Potrawa, Seelze (DE); Joachim Schulz, Pohle (DE)

(73) Assignee: Honeywell International Inc, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/595,002

(22) Filed: Nov. 8, 2006

(65) Prior Publication Data

US 2007/0051929 A1    Mar. 8, 2007

Related U.S. Application Data

(62) Division of application No. 10/499,865, filed as application No. PCT/EP02/14253 on Dec. 13, 2002, now Pat. No. 7,198,732.

(30) Foreign Application Priority Data

Dec. 21, 2001  (DE) ................. 101 63 295

(51) Int. Cl.
    *C09K 9/00* (2006.01)
    *G06K 19/14* (2006.01)
    *C07F 19/00* (2006.01)

(52) U.S. Cl. .............. 252/586; 235/491; 252/301.26; 252/588; 252/589; 534/16; 534/551; 546/2; 546/8; 546/156

(58) Field of Classification Search ........... 252/301.26, 252/62.56, 586, 588, 589; 534/16, 551; 235/491; 546/2, 8, 156
See application file for complete search history.

(56) References Cited

U.S. PATENT DOCUMENTS

| | | | |
|---|---|---|---|
| 4,833,311 A | 5/1989 | Jalon | 235/491 |
| 5,118,349 A | 6/1992 | Jalon | 106/21 |
| 7,198,732 B2 * | 4/2007 | Potrawa et al. | 252/301.26 |

FOREIGN PATENT DOCUMENTS

| | | |
|---|---|---|
| DE | 3032 611 A1 | 3/1981 |
| DE | 19512773 A1 | 10/1996 |
| GB | 2 128 985 A | 4/1983 |
| WO | WO 00/01663 | 1/2000 |

OTHER PUBLICATIONS

Cui, Jainzhong et al., Chemical Abstract Service, Columbus, Ohio, XP00223176 Abstract, 963-968 (1987).
E. P. Diamandis, Analyst, 117, 1879-1884 (1992).
G. A. Crosby et al., J. Phys. Chem., 66, 2493-2499 (1962).
G. Kallistratos, Chimika Chronika, New Series, 11, 249-266 (1982).
H.G. Brittain and F.S. Richardson, J. Amer. Chem. Soc. 99, 65-70 (1977).

* cited by examiner

*Primary Examiner*—Charanjit S Aulakh
(74) *Attorney, Agent, or Firm*—Carrie Beaths

(57) ABSTRACT

An article of manufacture marked with compositions comprising rare earth metal compounds which, due to their luminescence when irradiated with UV light, are suitable in particular for the marking of security-relevant items, such as documents or data carriers.

8 Claims, No Drawings

RARE METAL COMPOUNDS AND MIXTURES OF THESE

CROSS-REFERENCE TO RELATED APPLICATIONS

This application is a divisional of, and claims priority to, pending U.S. application Ser. No. 10/499,865, filed Jun. 21, 2004, which is a national stage entry of PCT Application No. PCT/EP02/14253, filed Dec. 18, 2002, which in turn claims priority to DE 101 63 295.9, filed Dec. 21, 2001.

BACKGROUND OF THE INVENTION

1. Field of the Invention

The present invention relates to rare earth metal compounds and mixtures of these which, due to their luminescence when irradiated with UV light, are very suitable for the marking of articles such as data carriers and documents.

2. Description of the Related Art

Fluorescent rare earth metal compounds, such as salts or complexes, are known from the prior art.

For applications in which a red fluorescent effect is required, europium diketonate complexes (see H. G. Brittain and F. S. Richardson, J. Amer. Chem. Soc. 99, 65-70 (1977)) and europium-carboxylic acid compounds (see G. Kallistratos, Chemiksa Chronika, New Series, 11, 249-266 (1982); E. P. Diamandis, Analyst, 117, 1879-1884 (1992)) have mainly been used up until now.

The europium diketonate complexes can be excited both in solid form and in the form of solutions or mixtures in organic solvents or polymer systems with UV light of a wavelength of 366 nm or 254 nm for the emission of an intensely red fluorescent light (see G. A. Crosby et al., J. Phys. Chem., 66, 2493-2499 (1962)). Soluble rare earth metal diketonate complexes are also known from U.S. Pat. No. 5,119,349. A decisive disadvantage of these complexes is however their low light stability and their low thermal stability.

Europium-carboxylic acid complexes generally have the desired thermal stability. However, it has been shown that, when these complexes are present in finely-distributed or amorphous form, an intense fluorescence can be achieved only upon irradiation with very short-wave UV light, e.g. with light of a wavelength of 254 nm. When grinding these carboxylic acid complexes, e.g. for the preparation of offset printing inks, there is thus a shift of the excitation maximum into the short-wave range i.e. the fluorescence intensity is clearly higher upon irradiation with short-wave UV light than upon irradiation with long-wave UV light. Furthermore, the luminescent effect in these complexes goes back to their crystal structure, as is known for the inorganic luminous pigments. A destruction of the crystals thus has a direct effect on the luminescence properties (see DE-A-30 32 611).

As a consequence of the aforementioned disadvantages of the known materials, the object of the present invention is to provide fluorescent rare earth metal compounds with the following properties:
- colorless in daylight
- high intensity of the emitted fluorescent light upon irradiation with UV light of a wavelength of 366 nm
- high thermal stability
- high light fastness
- no change in the fluorescence properties (intensity and CIE color coordinates) upon grinding.

SUMMARY OF THE INVENTION

This object is surprisingly achieved by rare earth metal compounds having at least one lanthanide metal and a 2-hydroxyquinoline-4-carboxylic acid having the formula:

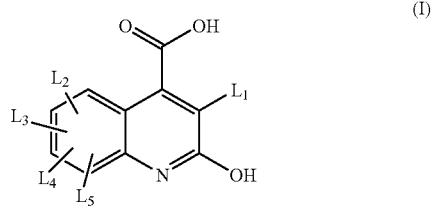

wherein $L_1$, $L_2$, $L_3$, $L_4$, and $L_5$ are independently selected from the group consisting of hydrogen, halogens, $C_1$-$C_6$ alkoxys, $C_1$-$C_6$ alkyls, $C_6$-$C_{12}$ aryls, —OH, —CN, $C_1$-$C_6$ alkylaminos, amides, and $C_1$-$C_6$ acyls; or by a rare earth metal compound having the formula:

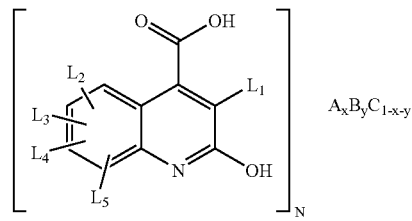

wherein:

$L_1$, $L_2$, $L_3$, $L_4$, and $L_5$ are the same as defined above,

A and B are independently selected from the group consisting of Eu, Th, Gd, Sm, Yb, Nd, La, and Ce;

A is not the same as B;

C is an alkaline earth metal selected from the group consisting of Ca, Sr, and Ba;

x is a positive number less than or equal to 1;

y is a positive number less than or equal to 1;

x+y is a positive number less than or equal to 1; and

N is equal to x+y+2;

or by the mixtures of these compounds.

The present invention further relates to a process for the preparation of the rare earth metal compounds and the mixtures of these having the step of reacting at least one lanthanide metal salt with the 2-hydroxyquinoline-4-carboxylic acid of formula I, and optionally, conducting the reaction in the presence of an alkaline earth metal salt. As used herein, the term "rare earth metal" means lanthanide metals.

The present invention further relates to a method of marking articles, such as electronic chip cards, check cards, credit cards, identity cards, bank notes, certificates, and the like, by applying the earth metal compound of the present invention to the article.

The present invention also relates to articles of manufacture that are marked by the aforementioned method of marking.

DETAILED DESCRIPTION OF PREFERRED EMBODIMENTS

The compounds according to the invention are rare earth metal compounds of at least one lanthanide metal and 2-hydroxyquinoline-4-carboxylic acid of formula (I)

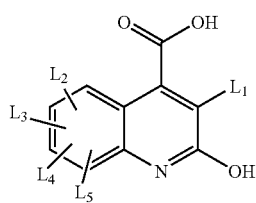

(I)

wherein $L_1$, $L_2$, $L_3$, $L_4$ and $L_5$, independently of each other, represent a substituent or H.

The compounds according to the present invention or mixtures of these are colorless under the action of daylight, but when excited with ultraviolet light they are fluorescent in different colors depending on the metal ion used. Due to these properties they can be used in a number of applications, and examples of possible fields of use are disclosed for example in DE-A-30 32 611.

The rare earth metal compounds according to the present invention are the result of extensive studies in the field of organic rare earth metal salts, in order to discover compounds capable of luminescence which also have the previously mentioned properties.

For this purpose, europium chelate complexes with differently substituted quinolinecarboxylic acids in particular were studied in more detail. Reference is made to Examples 1-11 and the Table 1 listed therein. It can be shown that the complexes with the majority of the studied quinolinecarboxylic acids tested still have the described disadvantages of the materials known from the prior art. On the other hand, it is surprising that only those complexes which are substituted in the 2-position of the quinolinecarboxylic acid by a hydroxy group have all the desired properties.

Preferred rare earth metal compounds and mixtures of these have at least two different rare earth metals. Such materials are able to emit different fluorescent light when the temperature is changed. This behavior and the resultant advantages when using the compounds and mixtures according to the invention in particular for marking and authentication, i.e. for establishing the genuineness of articles, are explained in more detail below.

Particularly preferred rare earth metal compounds and mixtures of these correspond to the general formula (II)

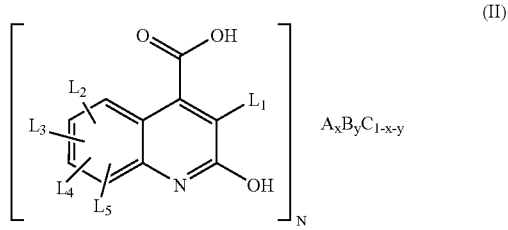

(II)

in which:

A and B represent different rare earth metals from the group europium, terbium, gadolinium, samarium, yttrium, neodymium, lanthanum and cerium, C is an alkaline earth metal from the group calcium, strontium and barium, $L_1$, $L_2$, $L_3$, $L_4$, $L_5$, independently of each other, represent a substituent or H, x+y results in a number which is greater than 0 and smaller than or equal to 1, and N=x+y+2.

It is to be taken into account that formula (II) simply states the ratio of the individual components of the components to each other. The nature of the bond between the 2-hydroxyquinoline-4-carboxylic acid and the metals has not yet been definitively clarified. It is, however, assumed that it is a complex-like bond and the 2-hydroxyquinoline-4-carboxylic acid and the metals are present as anions and as cations, respectively. In such a complex, a binding of the metals both via the carboxylate group, the hydroxy group, and the free electron pair of the nitrogen atom would be conceivable.

It is preferred that the rare earth metals A and B are selected independently of each other from the group consisting of europium, terbium, gadolinium and neodymium. It is particularly preferred that A or B represents europium or terbium.

Further tests surprisingly showed that, when two different rare earth metals are present, i.e. if x is greater than 0 and y is greater than 0, the compounds according to the invention emit, when excited with UV light, a fluorescent light the color of which depends on the temperature. Thus for example, compounds according to the invention which contain europium together with terbium showed upon irradiation with UV light at room temperature, an intense orange-red florescence which turns green upon cooling to −20 to −30° C. This surprising property of the emission of different fluorescent light depending on the temperature is very useful precisely when using the compound according to the invention for marking articles. In the case of conventional pigments which emit fluorescent light in a manner essentially independent of the temperature, articles, such as credit cards, marked with such a pigment can be tested only for this one type of fluorescent light by irradiation of the article with UV light. On the other hand, articles marked with the compounds according to the invention can in the case of reduction in temperature, e.g. by spraying with conventional cooling spray, emit a fluorescent light of a completely different color, and this behavior then confirms to the user that the tested article is actually marked and is thus authentic, i.e. genuine. The copying of the mark by forgers is thereby made additionally difficult.

It is further preferred that the substituents $L_1$, $L_2$, $L_3$, $L_4$, and $L_5$ present in the 2-hydroxyquinoline-4-carboxylic acid, independently of each other, represent H, halogen, $C_1$-$C_6$ alkoxy, $C_1$-$C_6$ alkyl, $C_6$-$C_{12}$ aryl, —OH, —CN, $C_1$-$C_6$ alkylamino, —CO—$C_1$-$C_6$-alkyl or —CO—NH$_2$.

The rare earth metal compounds according to the invention and mixtures of these are preferably prepared by reacting at least one rare earth metal salt with 2-hydroxyquinoline-4-carboxylic acid of formula (I) optionally in the presence of an alkaline earth metal salt. The rare earth metal salt is preferably a rare earth metal halide, such as europium chloride.

The reaction normally takes place in an aqueous medium and, in particular, in water.

Particularly preferably the 2-hydroxyquinoline-carboxylic acid is firstly reacted with alkaline substances to form 2-hydroxyquinoline-4-carboxylate. Potassium hydroxide or sodium hydroxide in particular, but also organic amines, such as ethanolamines or alkyl amines, are used as alkaline substances. Mixtures of alkaline substances can also be used.

The product which forms generally as a precipitate after the reaction is isolated in customary manner and dried and can then be used in this form for the planned applications.

The rare earth metal compounds according to the invention and mixtures of these show the aforementioned property of emitting fluorescent light in the visible range upon irradiation with UV light. In the case of the use of two different rare earth metals in the compounds or also in mixtures of compounds each with a rare earth metal, the particularly advantageous property can occur that the wavelength of the emitted fluorescent light depends on the temperature. In this way, a change in the color of the fluorescent light achieved upon irradiation with UV light at room temperature to another color is to be recognized when the material is cooled to lower temperatures.

The compounds according to the invention are also clearly more stable vis-à-vis solvents as they show a pigment-like character. Furthermore, the fluorescence properties of the compound and, in particular, the intensity of the emitted fluorescent light do not change when the compounds are ground. They are, moreover, thermally stable to a high degree and are as a rule colorless upon irradiation with daylight. Because of these properties, they can be used in a number of applications for luminescent substances. Examples of this are given in DE-A-195 12 773.

The rare earth metal compounds according to the invention and the mixtures of these compounds are preferably used for marking articles by providing the article with the compounds or the mixtures of these.

These articles are usually data carriers or documents, with chip cards, check cards or credit cards, being used in particular as data carriers, and identity cards, bank notes, and certificates as documents.

As the compounds according to the invention are colorless upon irradiation with daylight, they produce a marking which is not visible to the observer when used in this way, which is important for precisely these articles which, like chip cards, check cards or credit cards as well as identity cards, bank notes and certificates, are often-exposed to attempts at forgery. On the other hand, the irradiation of these objects with UV light produces a characteristic fluorescent light which, in the embodiment described above in more detail, changes color even when there is a temperature change, such as a cooling down, e.g. as a result of spraying of the item with a commercially available cooling spray. The colors of the fluorescent light produced in each case by special compounds according to the invention and mixtures of these at room temperature and at a changed, e.g. reduced temperature, is then a sure sign for the checker of a marked item, that the item was marked with the compounds. Consequently, the compounds according to the invention serve to prevent attempts at forgery or to detect attempts at forgery and to establish the genuineness of items.

The compounds according to the invention or mixtures of these can be incorporated in a customary manner into the articles to be marked. However, it is also conceivable to use them in the form of compositions which contain the compounds or mixtures of these together with a binder. In particular, acrylic polymers, polyamides, polyurethanes, polyesters and polyethylene terephthalates, as well as the corresponding monomers and oligomers, can be considered as binders. Customary auxiliaries can also be added to these compositions.

Furthermore, the compounds according to the invention can also be used in films, such as polymer films, or fibers such as spun-dyed fibers.

It is also conceivable that the compounds according to the invention can be used together with a liquid carrier, e.g. in the form of dispersions. Such dispersions can then be used for example to impregnate the items to be marked. Such a procedure is possible for the preparation of marked safety threads which are then incorporated into identity cards, bank notes, checks, and certificates.

Finally, the invention also relates to marked items which comprise the rare earth metal compounds according to the invention and mixtures of these.

The invention is explained in more detail in the following examples.

EXAMPLES

Examples 1 to 11

A series of compounds of europium and a quinolinecarboxylic acids having the formula:

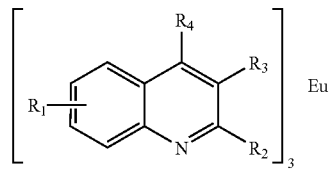

wherein R1, R2, R3, and R4 are substitutents as described in Table 1, were prepared to test the influence of the type of substitution of the quinolinecarboxylic acid on the properties of the compounds obtained.

The preparation of the compounds was carried out analogously to the instructions given below for examples 1 and 9.

The obtained quinolinecarboxylic acid europium compounds, which are presumably chelate complexes, were visually checked for the intensity of the fluorescent light emitted upon irradiation with UV light of a wavelength of 366 nm. In each case, the solid, a solution in toluene, and the composition coated onto a substrate which contained 5 wt. % of the compound in a binder system, were examined.

The UV stability of the prepared compounds was also tested by subjecting the prepared coatings in a SOL 2-apparatus from the company Dr. Höhnle to daylight D65 radiation for several hours and then visually checking under UV light the brightness of the fluorescent light emitted in each case and assessing the same by comparing the compounds with each other and with rare earth metal complexes known from the literature.

The results obtained are listed in the following Table 1.

TABLE 1

Comparison of Substituted quinolinecarboxylic acid europium compounds

| Example No. | R1 | R2 | R3 | R4 | Solution (Toluene) | Solid | Coating (5%) | UV Stability | Comments |
|---|---|---|---|---|---|---|---|---|---|
| 1 | —H | —OH | —H | —$CO_2H$ | --- | +++ | +++ | +++++ | |
| 2 | —H | —H | —OH | —$CO_2H$ | --- | --- | --- | --- | No fluorescence |
| 3 | —H | —$CH_3$ | —OH | —$CO_2H$ | --- | --- | --- | --- | No fluorescence |
| 4 | —H | —OH | —H | —H | --- | --- | --- | --- | No fluorescence |
| 5 | —H | —H | —H | —$CO_2H$ | --- | + | + | + | |
| 6 | —H | —H | —$CO_2H$ | —H | --- | + | + | + | |
| 7 | —H | —$CO_2H$ | —H | —OH | --- | + | + | + | |
| 8 | 8-OH | —$CO_2H$ | —H | —OH | --- | --- | --- | --- | No fluorescence |
| 9 | —H | -phenyl | —H | —$CO_2H$ | ++++ | +++ | +++++ | + | |
| 10 | —H | —$CO_2H$ | —H | —H | --- | ++ | ++ | + | |
| 11 | —H | —$CH_3$ | —OH | —$CO_2H$ | --- | -- | --- | --- | No fluorescence |

Key:
--- None
+ Very low
++ Low
+++ Satisfactory
++++ High
+++++ Very high

The following is to be deduced from the results given in the table.
1. Both the europium compounds with 3-hydroxyquinoline-carboxylic acid (Examples 2 and 3) and those with hydroxy-2-quinoline-carboxylic acid (Examples 7 and 8) show no, or only a very low, fluorescence.
2. If the hydroxy group is completely absent from the quinoline-carboxylic acid, then compounds with only a low intensity of the fluorescent light are obtained (Examples 5, 6 and 10). The only exception is the compound with 2-phenyl-4-quinoline-carboxylic acid (Example 9), which shows a very intense fluorescence both in solution and in the coating. This compound has, however, a decisive disadvantage in that it has only a very low UV stability, i.e. a very low light fastness.
3. The compound according to example 4 shows that only a slightly fluorescent compound is formed by the hydroxyl group in the 2-position alone.
4. Only the compound according to the invention according to example 1, in which both the hydroxy and carboxylic acid groups are present at the correct position in the quinoline moiety, shows the desired properties.

Example 1

A europium compound according to the invention was prepared.
To this end, 30 g (0.1585 mol) of 2-hydroxy-quinoline-4-carboxylic acid was suspended in 420 ml of water in a 1 L three-necked round-bottomed flask and dissolved by adding 6.34 g of sodium hydroxide.
A solution of 9.31 g of europium oxide in 15.64 g of 37 16 hydrochloric acid and 100 ml of water was added dropwise at 20-100° C., accompanied by stirring within 20 minutes, to the obtained clear solution.
The europium compound which then precipitated out was isolated and dried. It displayed a reddish-orange fluorescence upon irradiation with long-wave length W light (366 nm).

Examples 2-8

Examples 2-8 were prepared in a manner similar to preparation of Example 1.

Example 9

For comparison purposes, a europium-2-phenylquinoline-4-carboxylic acid compound was prepared.
To this end, 19.75 g (0.0792 mol) of 2-phenylcquinoline-4 carboxylic acid was dissolved in a 1 L three-necked round-bottomed flask in a solution of 5.23 g potassium hydroxide in 420 ml water.
A solution of 4.65 g of europium oxide in 7.95 g of 37% hydrochloric acid and 150 ml of water was added to this solution.
The compound, which then precipitated out, was isolated and dried. It was well soluble in customary organic solvents so that, in general, it would be possible to use it in printing systems which are still based on undesired organic solvents.
A very great disadvantage however is the pronounced migration from the binder used, as the compound is soluble, and the very low fastness to light, which manifests itself in a very marked fall in the intensity of the fluorescent light after irradiation with daylight.
The compound is therefore not suitable for external use.

Examples 12-15

Further rare earth metal compounds according to the invention or mixtures of these were prepared.
The materials obtained according to these examples possessed a pronounced pigment character, i.e. they are insoluble in customary organic solvents. Through suitable fine grinding, materials are obtained which are colorless under normal light but emit very strongly colored fluorescent light under UV light of 366 nm.
This makes it possible to produce, with the compounds according to the invention, all known printing systems, e.g.

water dilutable, oxidatively dried, and UV-reactive printing systems with high fastness to light.

Example 12

A europium-gadolinium compound according to the invention was prepared.

To this end, 30 g (0.1585 mol) of 2-hydroxyquinoline-4-carboxylic acid was dissolved in a 1 L three-necked round-bottomed flask in a solution of 6.34 g sodium hydroxide in 420 ml of water.

A solution of 8.376 g europium oxide and 0.959 g of gadolinium oxide in 15.64 g of 37% hydrochloric acid and 120 ml of water was added drop wise accompanied by stirring at 20-100° C. within 15-20 minutes to the obtained clear solution.

The compound which then precipitated out was isolated and died.

Example 13

A europium-terbium compound according to the invention was prepared.

To this end, 30 g (0.1585 mol) of 2-hydroxyquinoline-4-carboxylic acid was dissolved in a 1 L three-necked round-bottomed flask in a solution of 6.34 g of sodium hydroxide in 400 ml of water.

A solution of 8.376 g of europium oxide and 0.989 g of terbium oxide in 15.89 g of 37% hydrochloric acid and 100 ml of water was added drop wise accompanied by stirring at 20-100° C. within 30 minutes to the obtained solution.

The precipitate which then formed was isolated and dried. A specimen of the obtained compound showed, upon irradiation with W light of a wavelength of 366 nm, an intense orange-red fluorescence which changed to a green fluorescence when cooled to −20 to −30° C.

Example 14

A gadolinium-terbium compound according to the invention was produced.

To this end, 30 g (0.1585 mol) of 2-hydroxyquinoline-4-carboxylic acid was suspended in 400 ml water and dissolved by the addition of 10.46 g of potassium hydroxide.

A solution of 8.63 g of gadolinium oxide and 0.989 g of terbium oxide in 15.89 g of 37% hydrochloric acid and 100 g water was slowly added drop wise to this solution at 20-100° C. A fine precipitate thereupon formed which was isolated by extraction and then dried.

A specimen of the precipitate showed no visible fluorescence in a coating in water-dilutable acrylic varnish customary in the trade after drying and irradiation with UV light (366 nm). However, if the coating is cooled to approx. −20° C., an intense green fluorescence was visible.

Examples 15 and 16

In addition, for comparison purposes, metal compounds of cinnamic acid and 2-phenylquinoline-4-carboxylic acid with terbium-europium, and also gadolinium-europium and gadolinium-terbium were also prepared analogously to example 9.

However, none of the obtained compounds showed a change in color of the fluorescence upon irradiation with UV light of 366 or 254 nm, when cooled to −50° C.

What is claimed is:

1. An article of manufacture marked with the composition comprising:
   at least one lanthanide metal; and
   a 2-hydroxyquinoline-4-carboxylic acid having the formula

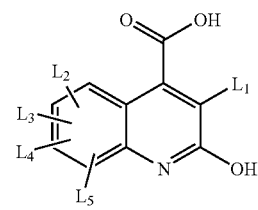

wherein $L_1$, $L_2$, $L_3$, $L_4$, and $L_5$ are independently selected from the group consisting of hydrogen, halogen, $C_1$-$C_6$ alkoxy, $C_1$-$C_6$ alkyl, $C_6$-$C_{12}$ aryl, OH, —CN, $C_1$-$C_6$ alkylamino, amide, and $C_1$-$C_6$ acyl.

2. The article of manufacture according to claim 1, wherein the lanthanide metal is selected from the group consisting of Eu, Tb, Gd, Sm, Yb, Nd, La, and Ce.

3. The article of manufacture according to claim 1, comprising at least two lanthanide metals.

4. The article of manufacture according to claim 3, wherein the lanthanide metals are selected from the group consisting of Eu, Tb, Gd, Sm, Yb, Nd, La, and Ce.

5. The article of manufacture according to claim 1, wherein said composition has a formula:

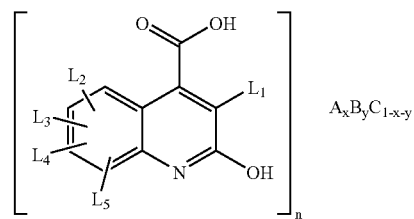

wherein,
A and B are independently selected from the group consisting of Eu, Tb, Gd, Sm, Yb, Nd, La, and Ce;
A is not the same as B;
C is an alkaline earth metal selected from the group consisting of Ca, Sr, and Ba;
x is a positive number less than or equal to 1;
y is a positive number less than or equal to 1;
x +y is a positive number less than or equal to 1; and
n is equal to x +y +2.

6. The article of manufacture according to claim 5, wherein x is greater than 0 and y is greater than 0.

7. The article of manufacture according to claim 5, wherein A and B are independently selected from the group consisting of Eu, Tb, Ga, and Nd.

8. The article of manufacture according to claim 7, wherein A is Eu and B is Tb.

* * * * *